United States Patent

Longo

(10) Patent No.: US 9,445,869 B2
(45) Date of Patent: Sep. 20, 2016

(54) MICROWAVE SURGICAL DEVICE

(75) Inventor: Iginio Longo, Rome (IT)

(73) Assignee: CONSIGLIO NAZIONALE DELLE RICERCHE, Roma (IT)

( * ) Notice: Subject to any disclaimer, the term of this patent is extended or adjusted under 35 U.S.C. 154(b) by 826 days.

(21) Appl. No.: 13/697,949

(22) PCT Filed: May 16, 2011

(86) PCT No.: PCT/IB2011/052133
§ 371 (c)(1),
(2), (4) Date: Feb. 21, 2013

(87) PCT Pub. No.: WO2012/007854
PCT Pub. Date: Jan. 19, 2012

(65) Prior Publication Data
US 2013/0144286 A1  Jun. 6, 2013

(30) Foreign Application Priority Data

May 17, 2010  (IT) .............. RM2010A0252

(51) Int. Cl.
*A61B 18/18* (2006.01)
*A61B 18/00* (2006.01)

(52) U.S. Cl.
CPC .. *A61B 18/1815* (2013.01); *A61B 2018/00023* (2013.01); *A61B 2018/00101* (2013.01); *A61B 2018/00244* (2013.01); *A61B 2018/00791* (2013.01); *A61B 2018/00821* (2013.01); *A61B 2018/1861* (2013.01); *A61B 2018/1884* (2013.01)

(58) Field of Classification Search
CPC ............... A61B 18/1815; A61B 2018/00023; A61B 2018/00101; A61B 2018/00244; A61B 2018/00791; A61B 2018/00821; A61B 2018/1861; A61B 2018/1884
See application file for complete search history.

(56) References Cited

U.S. PATENT DOCUMENTS

| | | | |
|---|---|---|---|
| 4,557,272 A * | 12/1985 | Carr | A61B 5/015 600/549 |
| 5,057,106 A | 10/1991 | Kasevich et al. | |
| 5,628,770 A * | 5/1997 | Thome | A61B 18/18 607/101 |
| 5,957,969 A | 9/1999 | Warner et al. | |
| 2002/0091427 A1 | 7/2002 | Rappaport et al. | |
| 2003/0060813 A1* | 3/2003 | Loeb | A61B 18/24 606/17 |

FOREIGN PATENT DOCUMENTS

| | | |
|---|---|---|
| EP | 1985253 A2 | 10/2008 |
| WO | 02061880 A2 | 8/2002 |
| WO | 2004037102 A1 | 5/2004 |
| WO | 2004084748 | 10/2004 |

\* cited by examiner

*Primary Examiner* — Amanda Patton
(74) *Attorney, Agent, or Firm* — Volpe and Koenig, P.C.

(57) ABSTRACT

A microwave surgical device with high energy efficiency produces, at an antenna, an asymmetric heating pattern directed towards the side and it comprises: a plain curved portion extending from the distal end of said external conductor; and an inflection point at said distal end of the external conductor, so that said curved portion has a single cavity directed towards the axis of the coaxial end part.

12 Claims, 7 Drawing Sheets

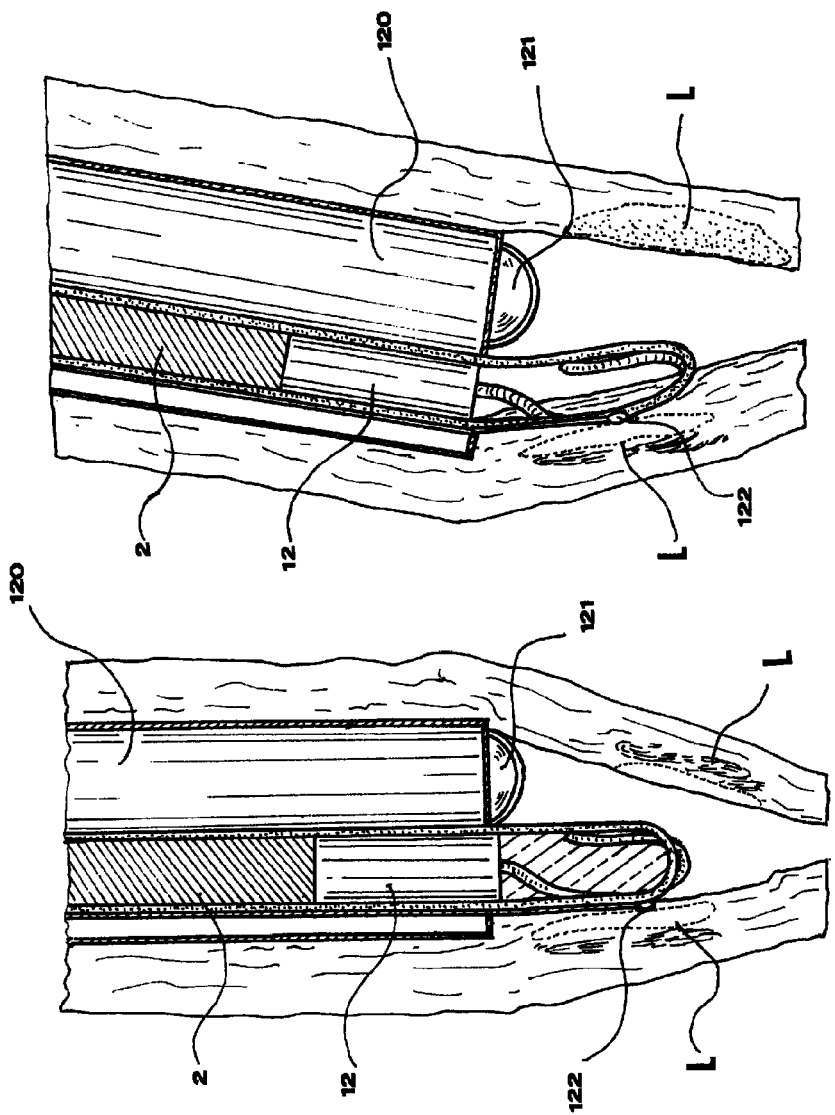
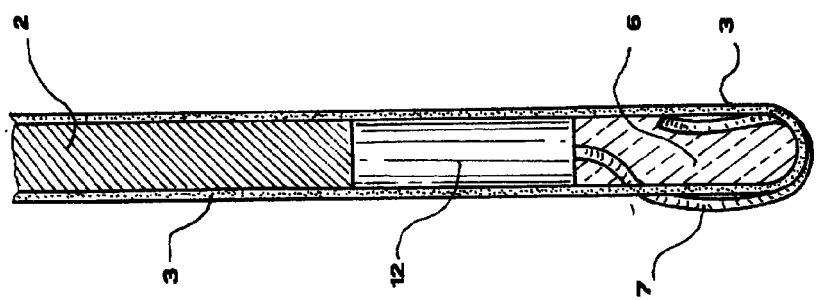
FIG. 17
FIG. 16
FIG. 15

MICROWAVE SURGICAL DEVICE

The present invention relates to a microwave surgical device, of the type comprising an antenna for emitting microwaves in a surgical site placed at the end of a transmission coaxial wire.

A device of this type is widely used in minimally invasive surgery for interstitial, percutaneous, endoscopic, laparoscopic and intra-surgical applications in the field of the so-called acute or thermoablative hypothermia, that is the localized heat application for ablating tissues. In particular, but not exclusively, the invention relates to the field of the interstitial application of microwaves in order to obtain the thermal destruction by means of thermocoagulation and/or thermo-ablation of lesions of biological tissues.

An example of interstitial application relates to the minimally invasive treatment of a natural cavity, such as for example the inner walls of the oesophagus, stomach, colon, bile ducts, vagina, etc.

However, it is meant that a device of such kind can be used even for the intra-surgical destruction of lesions with greater volume, by means of resection assisted by microwaves, wherein the device can act as a scalpel apart from as thermo-ablator.

Other devices operating in hypothermia are also known, with the application of electro-magnetic radiations in the field of radiofrequencies and of optical type (LASER) but, as it is known, the microwaves transfer heat to a tissue by exciting in particular the aqueous content thereof in a particularly efficient, rapid and deep way, without such application being influenced by the different tissue nature of the lesion, i.e. the tissue homogeneity thereof.

The typical frequency for the microwaves used with surgical purpose is 915 MHz or 2450 MHz (Iskander M. F. and Tumeh A. M., design Optimization of Interstizial Antennas, IEEE Transactions on Biomedical Engineering, 1989, 238-246), and in all other ISM (Industrial, Scientific and Medical) frequency bands assigned by the International Telecommunication Union (ITU) and reserved to the applications for industrial, scientific and medical use.

Examples of this kind of device are known from the application publications PCT Nr. WO 02/061880 and WO 2004/037102.

The generation of microwaves takes place by means of the particular shape of the transmission coaxial wire end, wherein the internal conductor or antenna can be shaped like a needle (dipole or linear monopole) extending from the end coaxial part deprived of the external tubular conductor. Microwaves are generated at the space existing between the projecting conductor and the external tubular conductor, therefore the heating pattern generally envelops the projecting internal conductor near the distal end of the external conductor, with a rotation symmetry and a substantially ellipsoidal shape.

As "heating pattern" the space near the emission is meant wherein the microwaves are efficient and where they determine then a real heating. This three-dimensional space, in case of action inside the homogeneous and isotropic tissues, is limited by isothermal surfaces having rotation symmetry around the axis of the coaxial cable.

It is meant then that the shape of such heating pattern influences notably the device functionality.

For this reason, several variants of the end extension have been proposed, each one characterized by a particular heating pattern.

However, in the intracavity applications, wherein the transmission wire is made to penetrate along a natural cavity, the lesions to be treated generally are arranged onto the surface of said cavity, then they are not necessarily arranged circumferentially, but laterally with respect to the end coaxial part.

Therefore, in the known variants, a heating pattern concentrated onto the tip or winding the end part could act not only on the lesion side, but circumferentially, and therefore even on the opposite side by causing a potentially relevant damage.

Furthermore, this or other configurations, producing a substantially symmetric and ellipsoidal or spheroidal heating pattern, are little efficient even from an energetic point of view, as great part of the microwaves on the side opposite to the operation one is substantially emitted uselessly.

Other configurations, for example providing the side tilting of the projecting tip, could obstruct, compromise or in any case complicate the introduction and the sliding of the end part inside the natural cavity.

A solution providing to make such end part deformable to direct its own tip towards the side could make the device structure extremely complex, even increasing the cross sizes of the end part.

In each case, endocavitary applications localized at great distance from the inlet hole generally would require very thin and very long wires, both aspects diminishing the available power to be supplied to the active end of the antenna.

Moreover, the fact of supplying the coaxial wire with a greater power would increase even the heat generated by the same transmission coaxial wire and this heat would be left in body portions which could be damage thereby.

The U.S. Pat. No. 4,557,272 describes a microwave terminal, wherein the internal conductor end projecting from the external conductor has a curved portion spaced apart from the external conductor end and isolated therefrom by means of a dielectric shield. Such shape does not allow determining an asymmetric and side heating pattern, but it concentrates the emission onto the terminal end.

Devices analogous to the previous one are described in the U.S. Pat. Nos. 5,957,969 and 5,057,106, in the US patent application Nr. 2002/091427, in the International application Nr. Publ. WO 2004/084748 and in the European patent application Nr. Publ. 1,985,253 A2, wherein the final end is coil-like shaped indeed to produce a heating pattern as symmetrical as possible.

In all these examples of the state of art, the feed point, that is the minimum distance point between internal and external conductor wherein the emitted power assumes the maximum value, is placed in a position on the symmetry axis of the external conductor and/or however very spaced apart from the end thereof, to make substantially symmetric and concentrated the microwave emission onto the antenna tip.

The technical problem underlying the present invention is to provide a microwave surgical device allowing to obviate the drawbacks mentioned by referring to the known art.

Such problem is solved by a device as specified above, which characterizes in that the antenna comprises:
- an inflection point at said distal end of the external conductor, and
- a curved portion which from said inflection point projects from the distal end of said external conductor;
- so that said curved portion is asymmetric and has a single cavity directed towards the axis of the coaxial end part, so as to determine a feed point, wherein the emitted power assumes the maximum value at a minimum distance between internal and external conductor, near said inflection point, in an asymmetric position with respect to the axis of the coaxial end part, providing a heating pattern the shape thereof is asymmetric with respect to the axis of the coaxial end part, substantially directed towards the side of the cylindrical projection of the coaxial end part opposed to the one thereto the coil curvature is directed after the inflection point.

The main advantage of the microwave surgical device according to the present invention lies in the fact of producing, at said antenna, an asymmetric and laterally protruding heating pattern. Furthermore, the emission of microwaves takes place with a high energy efficiency.

The present invention will be described hereinafter according to some preferred embodiments thereof, provided by way of example and not with limitative purposes with reference to the enclosed drawings wherein.

Figure 1:
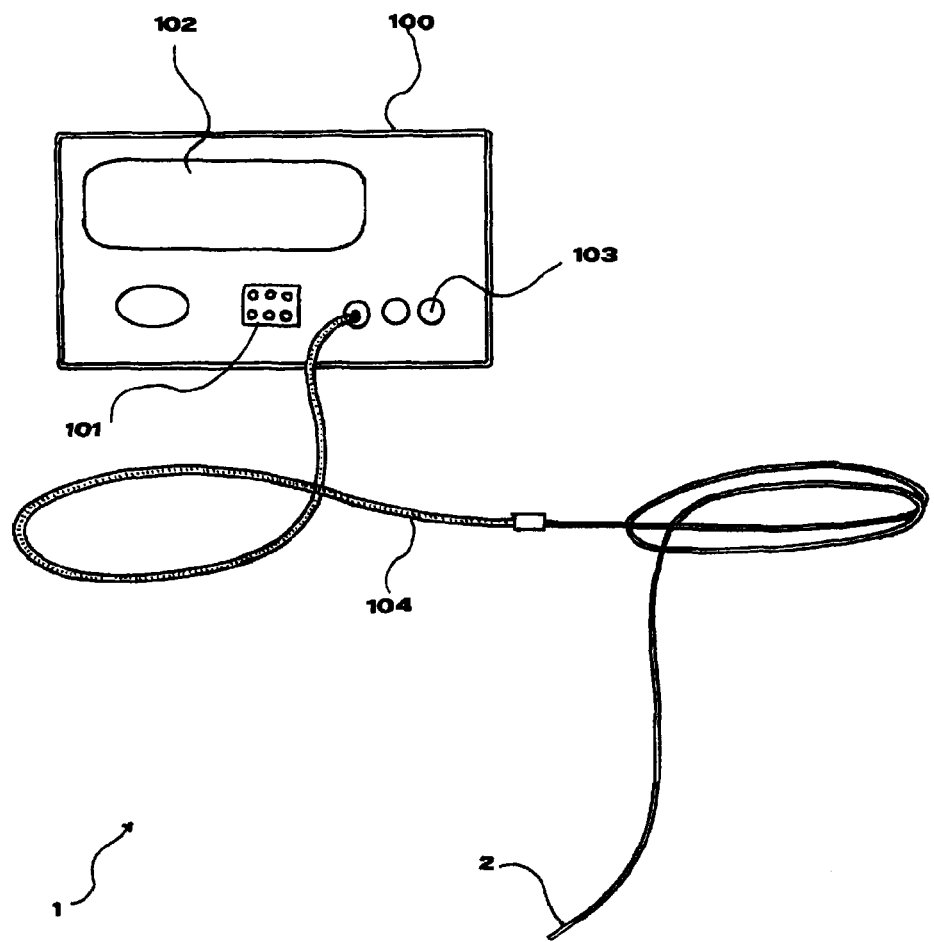
FIG. 1 shows schematically a microwave surgical device according to the invention, in its general configuration.

FIG. a 14 illustrates an additional operating mode of a device of one of the previous figures;

FIG. 15 shows an end coaxial part of the device of FIG. 1, implementing an eighth example of the present invention;

FIG. 16 illustrates an operating mode of a device with a coaxial end part as represented in FIG. 15 in a first configuration; and FIG. 17 illustrates the operating mode of FIG. 16 with the coaxial end part in a second configuration.

By referring to FIG. 1, a microwave surgical device is designated as a whole with 1.

It comprises a microwave generator 100 of the type with transistor or magnetron and programmable, equipped with a keyboard 101 as input means and a monitor 102 as output means.

Such programmable generator 100 can be of the type at the solid state with several output channels, with a characteristic impedance of 50Ω.

The emitted power can be pre-set by means of the keyboard and it can be adjustable, so that such generator 100 even constitutes means for adjusting the power emitted by the microwave antenna.

It has one or more output coaxial connectors 103 and one or more respective connecting coaxial wires 104, one in the present representation, to the distal end thereof an applicator is connected, that is an additional coaxial connection wire, which can be inserted into the operating channel of an endoscopic instrument, for the intracavitary, interstitial, percutaneous or intrasurgery insertion thereof.

This coaxial wire, operating as applicator, is of the type with low attenuation and it is flexible or substantially half-rigid, in order to ease the manoeuvre.

Said applicator ends with a coaxial end part 2 constituting the active end of the device 1 and which comprises, as it will be better clear hereinafter, a microwave source in the shape of an antenna.

Generally, but not exclusively, the antenna is the result of a modification of the end coaxial part 2, and in particular of the internal conductor thereof.

The so-far illustrated scheme is the general scheme of a microwave surgical device.

Figures 2, 3:
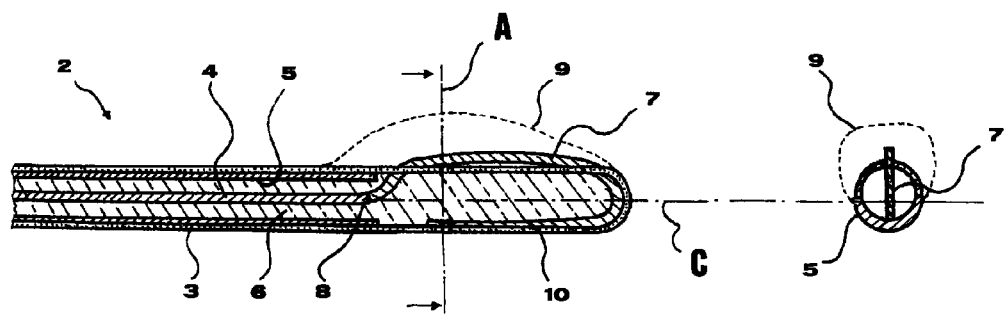
FIG. 2 shows an end coaxial part of the device of FIG. 1, implementing a first example of the present invention.
FIG. 3 shows a cross section of the end coaxial part represented in FIG. 2, taken according to the line A-A of FIG. 2.

By referring to FIG. 2 e 3, a first invention example is represented, by referring to a first variant of the coaxial end part 2.

It comprises a sheath 3 constituting the external casing of the part 2, closed at the final distal end of the end part 2.

It further comprises an internal conductor 4 of the wire-shaped type and a tubular external conductor 5, in a coaxial relation, with an insulating means 6 interplaced therebetween.

The internal conductor 4 extends beyond the distal end of the external conductor 5, thus forming an antenna 7 for emitting microwaves. The antenna 7 is shaped like a coil or half-coil, in the way which will be described hereinafter. Generally, it is possible showing the antenna 7 as connected to the internal conductor 4, in case the coil does not constitute a simple extension, but it is constituted by an added part.

The above-mentioned coil or half-coil comprises a curved portion extending by projecting from the distal end of said external conductor 5. Furthermore, the coil has an inflection point, designated with 8, which is placed substantially at said distal end of the external conductor 5.

Due to the inflection 8, the coil curvature changes: at first it is directed towards the outside but, from a near position, immediately adjacent to the distal end of the external tubular conductor 5, the coil curvature is directed in the opposite direction, that is towards the longitudinal axis C of the coaxial end part 2, which in turn represents the ideal continuation of the wire-shaped internal conductor 4.

At last, it is known that in the present example the coil has a curved portion projecting from the profile of the external tubular conductor 5 and even from the sheath 3. Said curved portion is entirely contained on the same one plane (which coincides with the plane of the drawing of FIG. 2) as well as, for functional reasons, the whole coil.

The coil planarity does not represent an essential feature for the correct operation of the here described device, but it represents an embodiment simple to be implemented.

The inflection position 8 is substantially fastened at the distal end of the external conductor, this means that the inflection could be slightly outside or slightly inside the external conductor.

As it can be seen in FIGS. 2 and 3, it determines a heating pattern 9 with particular shape, asymmetric with respect to the axis C of the coaxial end part 2, substantially directed towards the side of the cylindrical projection of the part 2 opposed to the one thereto the coil curvature is directed after the inflection point 8.

The inflection point 8 substantially implements the minimum distance point between internal conductor 4 and external conductor 5, therefore the power supply point of the emitted microwaves, called feed point, wherein the emitted power assumes the maximum value.

By summarizing, said curved portion is asymmetric and it has a single cavity directed towards the axis C of the coaxial end part 2, so as to provide a feed point which is near said inflection point, in an asymmetric position with respect to the axis C of the coaxial end part 2, considering that the inflection point 8 has the function of displace the internal conductor 4 from said axis C, so as to approach it asymmetrically to the end edge of the external conductor 5.

In this way, a heating pattern 9 is determined, the shape thereof is asymmetric with respect to the axis C of the coaxial end part 2, substantially directed towards the side of the cylindrical projection of the coaxial end part 2 opposed to the one thereto the coil curvature is directed after the inflection point 8.

As the inflection position is studied to implement a capacitive concentration at the minimum distance between antenna and end margin of the external conductor, the displacement of the feed point determined by the inflection position 8 with respect to the end edge point of the external conductor 5 nearest thereto is equal or lower than $\lambda/4$, wherein $\lambda$ is the wavelength of the chosen microwaves emitted by the antenna 7, by taking into account the dielectric permittivity within the antenna woks. In case of a frequency equal to 2450 MHz, $\lambda/4$ is equal to about 1 cm.

A greater distance outside between inflection and distal end would nullify the asymmetry efficiency of the heating pattern.

The position of the inflection point 8 is then brought nearer to the final end edge of the external conductor 5, in order to maximize the above-described effect, the useful length of the coil projecting from the external conductor 5 is substantially equal to $\lambda/4$, wherein $\lambda$ is the wavelength of the microwaves emitted by the antenna 7.

The thickness of the coaxial end part 2 can vary, in a purely exemplifying and not limiting way, from 0.5 mm to 3.0 mm, but it can vary from 2.5 mm to 10.0 mm for thermo-ablative applications with high power.

At the end of the curved portion, the coil has a twisted part 10 closing the coil towards the distal end of the external conductor 5, by conferring to the coil a closed geometry, in case of contact, or half-closed geometry.

With the above-described geometry, by applying a power of 15 W for 1 minute, it is possible obtaining the ablation of a lesion of the oesophageal mucosa which is 2.0 cm long, 0.5-cm wide and 2.5-mm thick.

Furthermore, applications on broader surfaces by means of sweeping action even on irregular outlines and surfaces, under endoscopic or laparoscopic or even visual control, in intrasurgery applications are possible.

In order to facilitate the sliding of the end part 2, both the sheath 3 and the dielectric material 6 insulating the two conductors 4, 5 can be made of polytetrafluoroethylene (PTFE) or other similar anti-adherent dielectric material. In any case the sheath 3 has to be made in an inert material.

The antenna represented in this case (FIGS. 2, 3) is of closed or half-closed type.

Figures 4, 5:
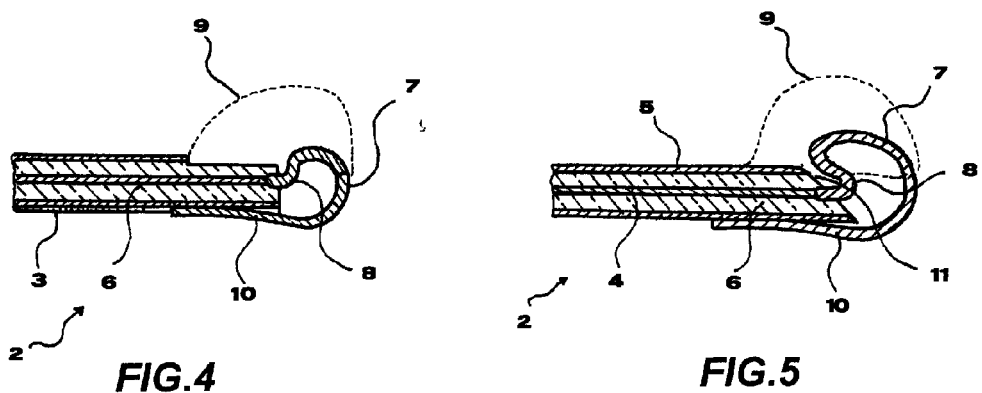
FIG. 4 shows an end coaxial part of the device of FIG. 1, implementing a second example of the present invention.
FIG. 5 shows an end coaxial part of the device of FIG. 1, implementing a third example of the present invention.

By referring to FIG. 4, showing a second embodiment example, the antenna 7 has an eyelet-like shape, whereas the sheath 3, at the curved portion of the antenna 7, is wholly absent, by leaving uncovered even the portion adjacent thereto of external tubular conductor 5.

This configuration has the effect of enhancing the local heating near the greatest emission point when conduction phenomena occur at the same heating pattern 9 when the antenna is in contact with organic tissues.

It is meant that, in this work hypothesis the nearer the antenna is to the end margin of the external conductor 5, the greater the conductive effect is obtained.

However, excessively reduced distances could cause a local carbonization of the tissues. At the usually used frequencies and for standard powers, such distance should not be lower than 2 mm.

FIG. 5 shows a third embodiment example similar to the previous one, wherein the antenna is very markedly bevelled shaped and wherein the maximum emission point, designated with 11, is not at the inflection point but it is on the curved part of the antenna 7, which is very near to the distal end of the external tubular conductor 5.

Again, this configuration has the effect of enhancing the local heating near the greatest emission point.

Figure 6:
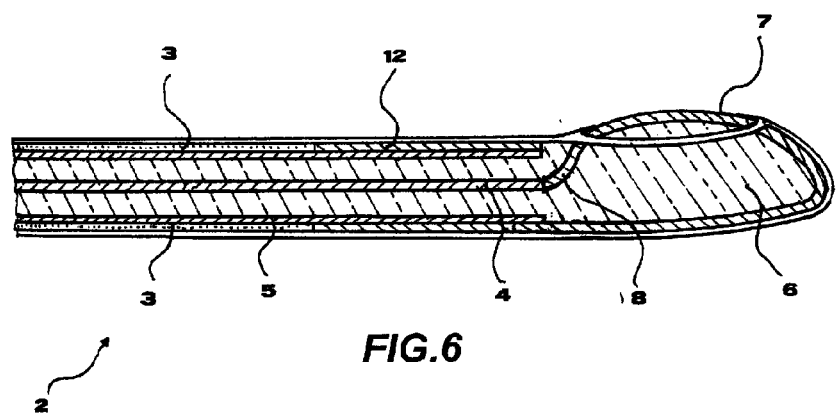
FIG. 6 shows an end coaxial part of the device of FIG. 1, implementing a fourth example of the present invention.

FIG. 6 shows a fourth embodiment example similar to the previous one. In this example the microwaves propagate in a flexible coaxial wire composed by a central conductor 4 and by an external conductor 5, separated by a dielectric 6, the external conductor 5 being protected by a sheath made of a plastic material and the end part of said sheath, at the respective distal end of the external tubular conductor 5, is removed and in its place there is a sleeve 12 made of rigid material, in particular metallic, conferring stiffness to the final portion of the coaxial end part 2, by allowing to keep in contact with greater efficiency the active end of the antenna 7 with the cavity wall by properly directing the tip of the endoscopic instrument.

Figure 7:
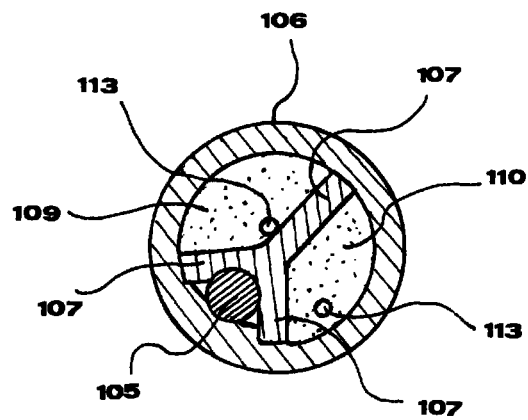
FIG. 7 shows a cross section of a connection wire, in a variant of the device of FIG. 1 implementing a fifth invention example, taken according to the line B-B of FIG. 8.
Figure 8:
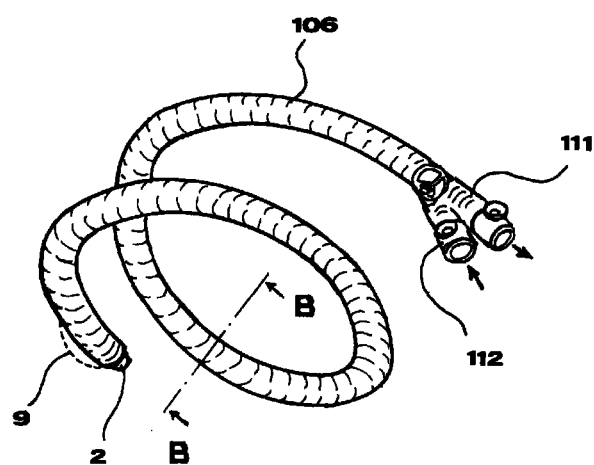
FIG. 8 shows a schematic perspective view of the connection wire of the variant of the device of FIG. 1, already represented in FIG. 7.

By referring to FIG. 7 e 8, a fifth embodiment example is described wherein the coaxial connecting wire 105 is inserted in a catheter 106 having a circular section and it is longitudinally divided into three portions by means of respective radial baffles 107 defining three corresponding channels.

The catheter 106 is flexible and made of suitable plastic material.

The coaxial wire ending with one of said herein described coaxial end parts 2 is housed in a first channel 105.

One or more temperature sensors can be housed in the same channel or in the surface thereof.

The second channel 109 and the third channel 110 are for circulating a coolant fluid, in particular water, poured through respective taps 111 and 112.

In this way, the heating along the coaxial wire in the first channel 105 is wholly nullified outside the catheter, due to the insulation given by the walls thereof and by the heat extraction through the refrigerating fluid.

To this purpose, inside the second and third channel 109, 110 suitable temperature sensors 113 can be inserted, for continuously controlling the extracted heat.

Figure 9:
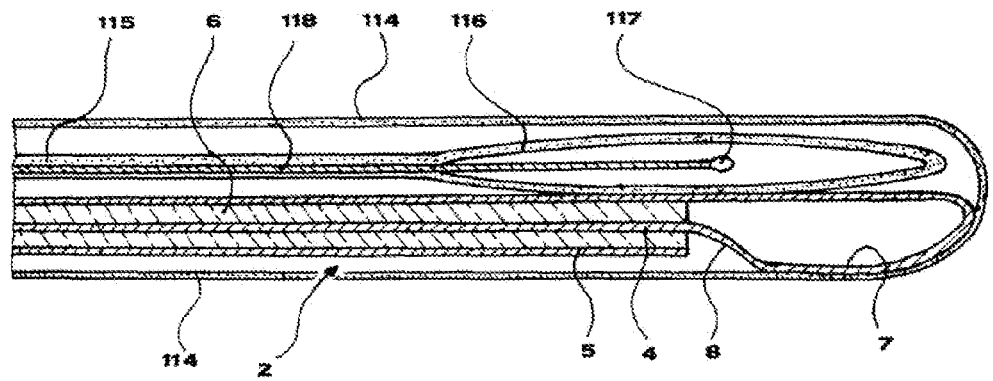
FIG. 9 shows an end coaxial part of the device of FIG. 1, implementing a fifth example of the present invention, in a first operating configuration.
Figure 10:
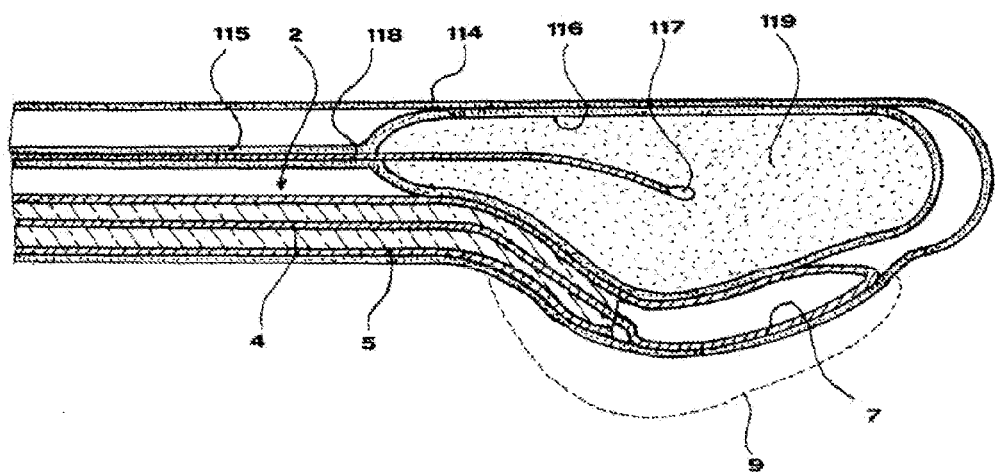
FIG. 10 shows the end coaxial part of FIG. 9 in a second operating configuration.

By referring to FIGS. 9 and 10, a sixth embodiment example is described wherein the coaxial wire and even the coaxial end part 2 are contained inside a flexible and inert tubular catheter 114 operating as external sheath.

It houses a duct 115 which is connected to a balloon 116 placed at the antenna 7, which can be of the type described by referring to FIGS. 2 and 3, that is wholly insulated and with closed coil.

A temperature sensor 117, constituted by a thermocouple or by a fibre optic sensor, connected to a control system through a transmission wire 118, a metallic or fibre optic wire respectively, passing through the above-mentioned conduit 115. is placed within the balloon 116.

The balloon 116 is placed in a position opposed to the one intended for the heating pattern 9. In this way, the temperature in opposite direction with respect to the operation one can be controlled with the sensor 117.

Beyond a determined threshold, or upon the emission of microwaves, a polar liquid 119, in particular water, can be poured-in for inflating the balloon 116 through the conduit 115.

The balloon inflation 116 protects and isolates the cavity wall opposed to the one of the operation and it bends the antenna 7 towards the operation direction, by improving the efficiency thereof.

The microwave application and the temperature sensor 117 keep the liquid temperature at a constant and programmable therapeutic value during the whole process.

Figure 13:
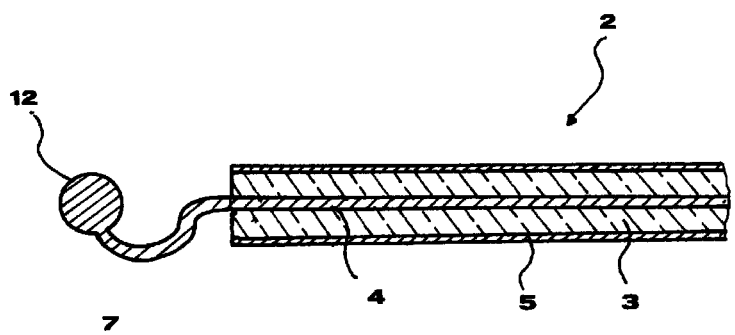
FIG. 13 shows an end coaxial part of the device of FIG. 1, implementing a seventh example of the present invention.

By referring to FIG. 13, a sixth embodiment example is described wherein the coil forming the antenna 7 is open, and the curved portion ends with a metallic sphere 12, made in a single piece with the internal conductor 4 for example by means of welding.

With this configuration, the antenna 7 has a smaller size, suitable to minimally invasive endocavitary applications, but with high powers.

The metallic sphere 12 allows concentrating the thermal effect, by reducing the length of the heating pattern. In this way, the overall length of the antenna 7 will result to be lower than $\lambda/4$.

Figure 11:
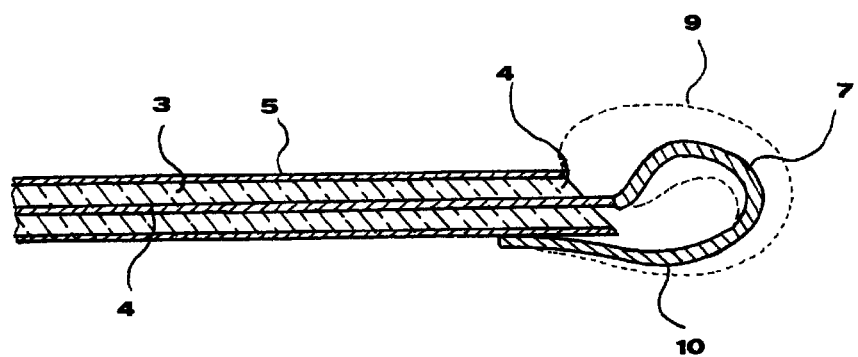
FIG. 11 shows an end coaxial part of the device of FIG. 1, implementing a sixth example of the present invention.

By referring to FIG. 11, an operating mode of the device according to the invention is illustrated, showing an antenna 7 shaped like an eyelet and of closed type.

In this configuration, the coil can have a lateral size greater than the one of the coaxial end part 2.

With powers as high as many tens of Watt at 2450 MHz, in particular for laparoscopic or intrasurgery applications, the antenna 7 can be shaped, at the extrados, so as to have a cutting edge.

In this way, the instrument can be used to perform simultaneously the cutting and the coagulation. This can be useful to obtain a resection assisted with microwaves, wherein the antenna 7 acts even as a scalpel, even of great fragile and vascularized masses therefor a traditional resection could be dangerous.

Figure 12:
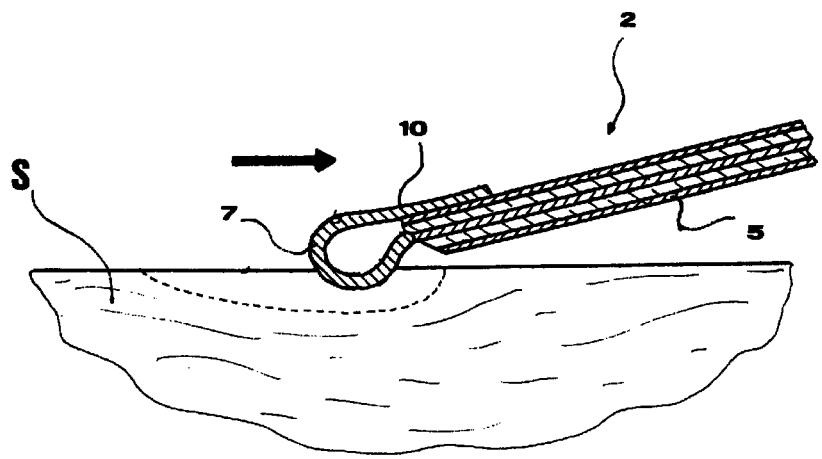
FIG. 12 illustrates an operating mode of a device of one of the previous figures.

In FIG. 12 the way of operating on a lesion of surface S is illustrated, by performing a surface resection thereof, with a cutting direction parallel to the lesion surface and with a simultaneous coagulation.

Figure 14:
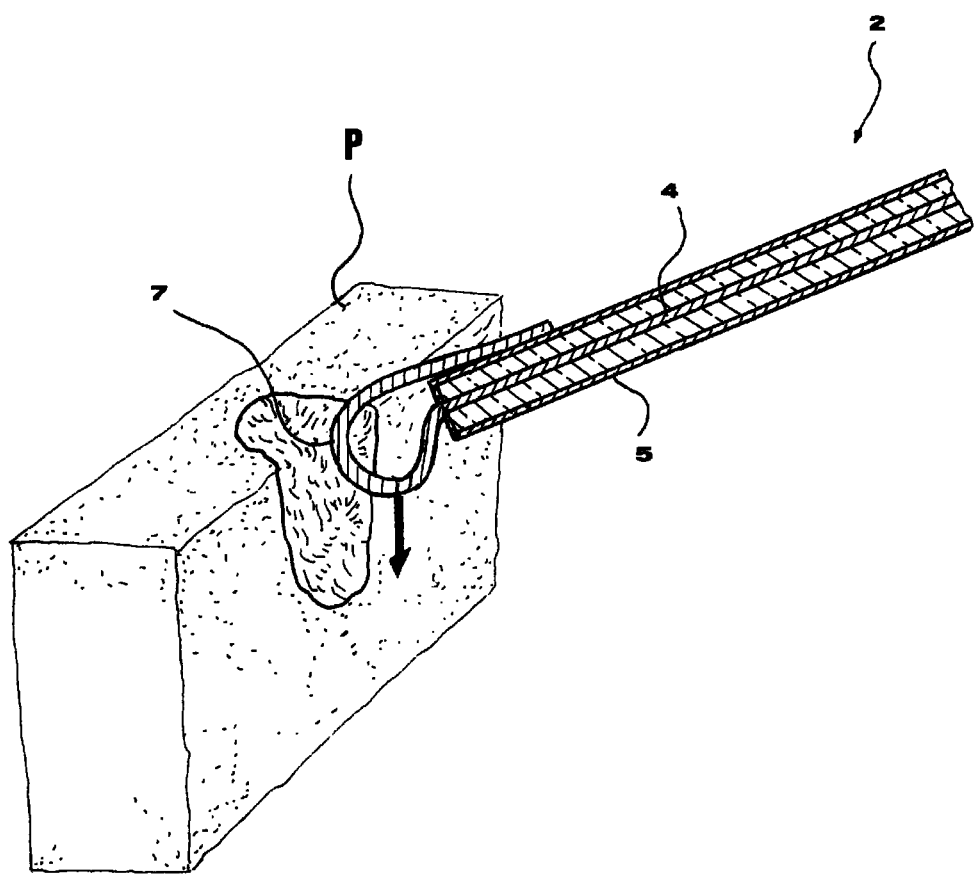

In FIG. 14 the way of performing a coagulation and the cutting of a volume of an hepatic parenchyma P with pyramidal shape is illustrated, by applying for example a power of 80 W at 2450 MHz.

By referring to FIGS. 15, 16 and 17 a seventh embodiment example of the device is described, wherein the coaxial end part 2 is inserted into the channel of a tubular endoscope 120 at the end thereof there is an optical objective lens 121.

The end part 2 of FIG. 15 is analogous to the one described by referring to FIG. 6, wherein the used sheath is however of thermo-reducing type and it covers the whole end part 2, even the distal end thereof. The antenna 7 is partially exposed in the maximum emission point.

The sleeve 12 allows to bring the end part 2 in strict contact with the internal wall of the cavity wherein it has to operate, by rotating the end of the endoscope 120 at the same time and in a suitable way.

An additional sensor 122 to detect the temperature through the channel of the endoscope 120 could be present. Furthermore, it is possible making use of means to obtain an ultrasonographic image of the operation area.

It can be appreciated that, thanks to the endoscope vision, it is possible rotating the instrument to operate on lesions L on opposite walls of the operated cavity, for example an oesophagus.

By summarizing, by way of example and without expecting to exhaust the list, some treatment applications relate to:
removal of the atrioventricular conduction defects of the myocardium in arrhythmia and thermo-ablative treatment of atrial fibrillation;
palliative treatment of osteolytic lesions in the skeleton tumours;
removing obstructions from stenosing lesions allowing the passage of a thin applicator;
palliation of rectum lesions in pelvic freezing or in chronic or acute bleeding;
palliation or treatment in acute benign or malignant bleeding gastric lesions;
treatment of papillary lesions, by using the active coil (in this case placed outside the sheath), even to surround and destroy thermally the peduncle of a protuberance;
laparoscopic treatment of neoplasia with lesion extended necrosis and with drainage of lymph nodes;
hypothermal treatment, by means of direct action of the microwaves, of surface lesions of the internal wall of circumferential and not circumferential natural cavities, with temperature thermometric control and ultrasonographic, even endoscopic, control of the wall thickness;
heating of the mucosa of the internal wall of natural cavity obtained by means of a plastic catheter equipped with an inflatable balloon, filled-up with liquid, as illustrated in FIG. 10;
resection of massive solid lesions assisted by microwaves, obtained by means of a power applicator having the active end configured like an asymmetric coil so as to concentrate the thermal effect in the tissue in direct contact with the maximum emission area.

The shown applicator could be developed and engineered as coagulating instrument available for endoscopes equipped with operating channel. It could also be an integral part of endocavitary catheters for the controlled treatment of wall lesions, both with thermo-ablative action and for multimodal uses, that is wherein the strongly localized thermal treatment is used advantageously to enhance the concomitant effect of ionizing or chemotherapeutic radiations, obtaining better results with smaller doses (chemo-radio-thermo-therapy).

To what described above a person skilled in the art, in order to satisfy additional and contingent needs, can introduce several additional modifications and variants, all however within the protective scope of the present invention, as defined by the enclosed claims.

The invention claimed is:

1. A microwave surgical device (1), comprising:
a transmission line having a coaxial end part (2) with an internal wire-shaped conductor (4) and an external tubular conductor (5); and
an antenna (7) for emitting microwaves connected to a distal end of the internal conductor (4), the antenna (7) comprising:
an inflection point (8) at said distal end of the external conductor (5); and
a curved portion projecting from said inflection point (8) and forming a coil with a coil curvature,
so that said coil is asymmetric and forms a single cavity, defined by said coil curvature, directed towards an axis (C) of the coaxial end part (2), so as to determine a feed point, wherein an emitted power assumes a maximum value at a minimum distance between internal and external conductor (4, 5), proximate to said inflection point (8), in an asymmetric position with respect to the axis (C) of the coaxial end part (2), providing a heating pattern (9) with a shape that is asymmetrical with respect to the axis (C) of the coaxial end part (2) and protrudes laterally.

2. The device according to claim 1, wherein a displacement of the feed point determined by the inflection point (8) with respect to an end edge point of the external conductor (5) nearest thereto is equal to or lower than $\Delta/4$, wherein $\lambda$ is a wavelength of the microwaves emitted by the antenna (7).

3. The device according to claim 1, wherein said curved portion lies wholly on a plane.

4. The device according to claim 1, wherein a length of the coil projecting from the external conductor (5) is substantially equal to $\lambda/4$, wherein $\lambda$ is the wavelength of the microwaves emitted by the antenna (7).

5. The device according to claim 1, wherein the coil of the antenna (7) has a lateral size greater than one of a coaxial end part (2).

6. The device according to claim 1, wherein the coaxial end part (2) is wound on a sheath (3) which, at the curved portion of the antenna (7), is wholly absent so as to leave uncovered even the portion of external tubular conductor (5) adjacent thereto.

7. The device according to claim 1, wherein the coil is bevelled shaped.

8. The device according to claim 1, wherein a sleeve (12) made of rigid material is provided, at the respective distal end of the external tubular conductor (5), to confer stiffness to the end portion of the coaxial end part (2).

9. The device according to claim 1, wherein the coaxial connection wire is inserted in a catheter (106) having a circular section and being longitudinally divided into three portions by means of respective baffles (107) defining three corresponding channels:
  a first channel (105), wherein said coaxial wire ending with a coaxial end part (2) is housed;
  a second channel (109); and
  a third channel (110) for circulating a coolant fluid.

10. The device according to claim 9, wherein temperature sensors (113) for continuously controlling the extracted heat are inserted within the second and third channel (109, 110).

11. The device according to claim 1, wherein the coaxial wire and the respective coaxial end part (2) are housed within a flexible tubular catheter (114) configured as an external sheath, housing a conduit (115) which is connected to a balloon (116) placed at the antenna (7), wherein:
  a temperature sensor (117) is placed within the balloon (116);
  the balloon (116) is placed in a position opposed to the curved portion;
  a cooling liquid (119) configured to be poured-in for inflating the balloon (116) through the conduit (115),
the balloon (116) inflation protects and isolates the cavity wall opposed to the one of the operation.

12. The device according to claim 4, wherein the coil forming the antenna (7) is open and the curved portion ends with a metallic sphere (12), an overall length of the antenna (7) being lower than $\lambda/4$.

* * * * *